United States Patent
Ali

(10) Patent No.: US 8,888,485 B2
(45) Date of Patent: *Nov. 18, 2014

(54) DEVICES AND METHODS FOR ENHANCING BONE GROWTH

(71) Applicant: Mohamed Ikbal Ali, San Francisco, CA (US)

(72) Inventor: Mohamed Ikbal Ali, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/919,827

(22) Filed: Jun. 17, 2013

(65) Prior Publication Data

US 2013/0280675 A1  Oct. 24, 2013

Related U.S. Application Data

(63) Continuation of application No. 13/335,371, filed on Dec. 22, 2011, now Pat. No. 8,485,820.

(51) Int. Cl.
| | | |
|---|---|---|
| *A61C 13/225* | (2006.01) | |
| *A61C 13/00* | (2006.01) | |
| *A61B 6/14* | (2006.01) | |
| *A61C 8/00* | (2006.01) | |
| *A61C 8/02* | (2006.01) | |
| *A61K 6/06* | (2006.01) | |
| *A61K 6/04* | (2006.01) | |
| *A61B 6/03* | (2006.01) | |
| *A61F 2/28* | (2006.01) | |
| *A61F 2/30* | (2006.01) | |

(52) U.S. Cl.
CPC ........... *A61C 8/0009* (2013.01); *A61C 13/0004* (2013.01); *A61B 6/14* (2013.01); *A61C 8/0027* (2013.01); *A61C 8/0031* (2013.01); *A61C 8/005* (2013.01); *A61C 8/0006* (2013.01); *A61K 6/0681* (2013.01); *A61F 2002/2889* (2013.01); *A61F 2/2803* (2013.01); *A61K 6/04* (2013.01); *A61C 13/0018* (2013.01); *A61B 6/032* (2013.01); *A61C 8/008* (2013.01); *A61F 2002/30578* (2013.01); *A61F 2002/2835* (2013.01); *A61F 2/2875* (2013.01)
USPC ........................................................ 433/173

(58) Field of Classification Search
USPC ........... 433/172–176, 201.1, 202.1, 215, 220, 433/221; 623/16.11
See application file for complete search history.

(56) References Cited

U.S. PATENT DOCUMENTS

| | | |
|---|---|---|
| 5,006,070 A | 4/1991 | Komatsu |
| 5,306,149 A | 4/1994 | Schmid et al. |

(Continued)

OTHER PUBLICATIONS integral. (n.d.). Dictionary.com Unabridged. Retrieved Oct. 31, 2013, from Dictionary.com website: http://dictionary.reference.com/browse/integral.*

Zimmer Holding, Inc., Clinical Advantages of Trabecular Metal™ Technology Demonstrated in New Studies http://www.zimmer.com/en-US/hcp/news/news-02-17-2011-clinical-advantages-of-trabecular-metal.jspx, Feb. 17, 2011, San Diego, CA.

International Search Report and Written Opinion of the International Searching Authority, on PCT application No. PCT/US2012/070886, dated Feb. 25, 2013, 9 pgs.

*Primary Examiner* — Heidi M Eide

(74) *Attorney, Agent, or Firm* — Soody Tronson Law Group (STLGip

(57) ABSTRACT

The present invention is generally related to implants for compensating bone loss in mammalian body, and to devices and methods for replacing or creating facial bone. The present invention relates to devices and methods for implanting an implantable device in a subject's body. The implantable device embodying features of the present invention include a body formed from a rig or matrix having a trabecular meshwork structure or cells with shapes suitable for a particular anatomical area of interest. The device may be a dental implant serving as a platform for placement of dental crowns.

9 Claims, 14 Drawing Sheets

(56) References Cited

U.S. PATENT DOCUMENTS

| | | |
|---|---|---|
| 5,769,637 A | 6/1998 | Morgan |
| 6,030,218 A | 2/2000 | Robinson |
| 6,328,765 B1 | 12/2001 | Hardwick et al. |
| 6,379,962 B1 | 4/2002 | Holy et al. |
| 2005/0010304 A1 | 1/2005 | Jamali |
| 2007/0248933 A1 | 10/2007 | Rutherford et al. |
| 2007/0269769 A1 | 11/2007 | Marchesi |
| 2009/0215007 A1 | 8/2009 | Caterini et al. |
| 2009/0291415 A1 | 11/2009 | Binderman et al. |
| 2010/0137990 A1 | 6/2010 | Apatsidis et al. |
| 2010/0161061 A1 | 6/2010 | Hunt |
| 2010/0256773 A1 | 10/2010 | Thijs et al. |

* cited by examiner

DEVICES AND METHODS FOR ENHANCING BONE GROWTH

RELATED APPLICATIONS

This application is a continuation of, and claims priority from, U.S. patent application Ser. No. 13/335,371, filed Dec. 22, 2011, now U.S. Pat. No. 8,485,820, incorporated herein by reference in its entirety.

FIELD OF THE INVENTION

The present invention is generally related to implants for compensating bone loss in the mammalian body, and more particularly, and for example devices and methods for replacing or creating facial bone.

All patents and published patent applications referred to herein are incorporated by reference in their entirety.

BACKGROUND

Bone loss is a phenomenon that may occur for any number of reasons during one's life (whether human, mammal, or any other vertebrate). Dental implants are fixtures of metal, typically titanium alloy, which are surgically screwed into the jawbone, often for replacing missing teeth. In the case of a dental implant, the implant is an anchor for a naturally-appearing false tooth or a set of false teeth. The success rate of dental implants depends on where and how the implants are placed and their purpose. It is important that the subject has enough bone in the area of the missing tooth/teeth for the implants to be attached to. Implants are used to replace single, multiple or all teeth. Implants are increasingly being used to replace fixed bridges and removable partial or full dentures.

For a patient who is missing one or more of his/her teeth, implants may well be an option for candidate as long as the patient has enough bone in the area of the missing tooth/teeth to facilitate the anchorage of the implants. If the patient does not have enough bone for this purpose, a bone graft may be necessary. Dental implants are alternatives to fixed bridge, a removable partial dentures or removable full dentures.

The typical implant procedure is a surgical placement of the implant or implants in the patient's jawbone which requires a three to six months healing period before the implant restoration (crown) can be placed. During this healing time, the bone grows in and around the titanium implant creating a very strong support. Although the rejection or failure rate of dental implants is low, in the event such rejection happens, the implant is replaced with another implant of a slightly larger size or do bone graft and place another implant When missing one tooth, the cosmetic dentist may use a flipper to fill the space. A flipper is a false tooth to temporarily take the place of a missing tooth before the permanent crown is placed on the implant. A flipper can be attached via a wire or an acrylic base that fits on the roof of the mouth. Flippers are meant to be a temporary solution while awaiting the permanent crown to be placed on the implant(s).

There are many implants available, each designed for a specific function. Most are made of titanium alloy, an inert metal which has been proven to be effective at fusing with living bone, a process known as osseointegration.

Sometimes, when resorption has excessively reduced the jawbone, it can be rebuilt through modern bone grafting techniques. Bone grafts can build up or fill in jawbone defects allowing the placement of dental implants.

In the single surgery method the dentist will order a special CAT scan of the patient's jawbone. Using the CAT scan data and advanced computer modeling techniques, a model of the jawbone is constructed. This model is used by a dental laboratory to fabricate the custom subperiosteal implant to fit the subject's jaw. A surgical procedure is then carried out where the jawbone is exposed and the implant placed. The gums are closed with several stitches and the replacement teeth are placed on the abutments of the subperiosteal implant.

Despite the advances in dentistry and implant procedures, there is room for further improvement in providing enhanced devices and methods for more timely placement of implants, in particular dental implants.

SUMMARY OF THE INVENTION

The present invention relates to devices and methods for implanting a device in a patient's body. In an embodiment, the implantable device embodying features of the present invention include a body formed from a rig having a trabecular meshwork structure with shapes suitable for a particular anatomical area of interest. In an embodiment, the device is a dental implant serving as a platform for placement of dental crowns or bridges. In an embodiment, the present devices and methods enhance the growth of bone, as for example, the mandibular bone. In an embodiment, the growth is new bone growth where for any number of reasons, the original bone was either lost or never existent. Provided herein is an implantable device comprising a 3 dimensional trabecular meshwork structure having a length, a height, a width, a first end, and a second end, at least one fixating surface for receiving a fixating element for operatively attaching the rig to the bone and at least one cap receiving surface for receiving one or more caps thereon. In some embodiments of the device, the length of the structure is nominally defined by a distance between the first end and second end of the structure, and ranges from about 5 mm to about 200 mm. In some embodiments of the device, the height of the structure is nominally defined by a distance between a lower rim and an upper rim of the structure, and ranges from about 1 mm to about 60 mm. In some embodiments of the device, the structure is formed from a plurality of cell structures. In certain embodiments of the device, the plurality of cell structures comprises a matrix having a depth and height which ranges from about 1 to about 9 cells, and from about 9 to about 1 cell, respectively. In some embodiments of the device, each cell has an inner surface area ranging from about 50 microns to about 10 mm. In other embodiments of the device, the ratio of the total inner area of the cells to the total surface area of the structure ranges from about 10% to about 90%. In some embodiments of the device, the lower rim of the structure includes at least one bone fixation surface. In certain embodiments of the device, at least one cap receiving surfaces include at least one abutment receiving surface for receiving a crown thereof Also provided is a method for implanting a device in a patient's body, comprising identifying a patient suitable for receiving an implant such as a dental implant, commissioning a three dimensional image of a target area of the patient's body for receiving the implant, commissioning a design of the implant using computer modeling, commissioning the construction of the implant using deposition method, and affixing the implant within the patient's body. In some embodiments of the method, the image is procured using CT scan. In other embodiments of the method, the implant is constructed using a 3D laser printing techniques by 3D Laser Sintering Printing. In certain embodiments of the method, the implant is constructed from a bio-compatible material. In some embodiments of the method, the bio-compatible material comprises at least one of titanium alloy or zirconium. In an embodiment, the implant material of the present invention is non-porous or substantially non-porous. In an embodiment, the surface of the implant is textured in areas where bone growth is desirable to maximize the surface between the bone and the rig. In an embodiment, where the abutment emerges through the soft tissue, the implant surface is smooth to minimize undesirable bacteria collection at the soft tissue level (e.g., gum level).

In other embodiments of the method, the implant is a dental implant and the affixing of the implant within the patient's body comprises reflecting a gum of the patient to expose a bone area suitable for receiving the dental implant, disposing a dental implant on the bone area, the dental implant comprising a rig having a three (3) dimensional trabecular meshwork structure having a length, a height, a width, a first end, and a second end, at least one fixating surface for receiving a fixating element to operatively attach the rig to the patient and at least one cap receiving surface for receiving one or more caps thereon. In an embodiment the rig has a plurality of cells forming the meshwork and facilitating the fixation of the dental implant to the patient's bone. In certain embodiments, the method further comprises applying bone graft substance to the plurality of the cells. In some embodiments, the method further comprises disposing at least one permanent abutment on a pre-determined portion of the cap receiving surface fixating the gum in place, and disposing one or more caps on the at least one permanent abutment. In other embodiments of the method, disposing of the permanent abutment occurs during at least substantially the same surgical procedure as the disposing of the rig in the patient's mouth. In some embodiments of the method, disposing of the permanent abutment occurs in a substantially subsequent surgical procedure following the disposing of the rig in the patient's mouth after the passage of a period of time. In certain embodiments of the method, the subsequent surgical procedure comprises, disposing healing abutments onto the rig, and allowing passage of time before disposing the permanent abutment step.

The rig being a three dimensional structure, includes several sides, surfaces, and/or ends, herein described relative to a patient's mouth once implanted therein. It should, however, be appreciated by those skilled in the art that such relative positional references are for ease of reference.

In an embodiment, the rig includes a length, a height, a width, a front end or edge, and a back end or edge, an outer surface, and an inner surface. These nouns describing the various parts of the device are used for ease of reference and are as defined by the present inventor. By way of example, as used herein and as positioned in the lower jaw of a patient's mouth, the front end refers to the side closest to the patient's front teeth; back end refers to the end opposite the front end; outer surface refers to the side of the device facing the cheek of the patient; the inner surface refers to the side of the device opposite the outer surface; the length refers to the dimension extending from the front end (toward the front tooth) to the back end (toward the molar tooth); height refers to the dimension extending vertically from the surface adjacent the lower jaw toward the roof of the mouth; width refers to the dimension extending between the outer surface and the inner surface. It should be noted that although the present invention is being described relevant to a dental implant and process for making and using the same, that such devices and methods are not limited to the dental applications and may be used in any other anatomical structure suffering from some, substantial, or complete bone decay or bone loss, or insufficient bone mass.

The length of the structure may nominally be defined by a distance between the first end and second end (or rim) of the structure, and ranges from any amount to fit within a patient's mouth. For example, the range of length may be from about 5 mm to about 200 mm. In other embodiments of the device, the height of the structure may be nominally defined by a distance between a lower rim and an upper rim (or lower edge and upper edge) of the structure, and ranges from any amount to fit within a patient's mouth. For example, the range of height may be from about 1 mm to about 60 mm. In some embodiments of the device, the structure may be formed from a plurality of cell structures. In certain embodiments of the device, the plurality of cell structures comprises a matrix having a depth and height which ranges from any amount to fit within a patient's mouth. For example, the range of depth and height may be from about 1 to about 9 cells. The range of depth and height may also, for example, range from about 9 to about 1 cell. In other embodiments of the device, each cell has an inner surface area ranging from any amount to fit within a patient's mouth. For example, the inner surface area range may be from about 50 microns to about 10 mm. In other embodiments of the device, the ratio of the total inner area of the cells to the total surface area of the structure may range from any amount to fit within a patient's mouth. For example, the ratio of the total inner area of the cells to the total surface area of the structure may range from about 10% to about 90%.

The matrix, having a plurality of cell structures, may also be referred to as a rig, platform, device, implant, mesh network, meshwork, scaffolding, structure, metallic bridge, plate, or combinations thereof. The matrix may also be made of any type of suitable material.

The implant includes at least one bone fixation feature for being operatively attachable to a bone surface of the patient. The implantable device, in an embodiment, includes at least one cap (or similar coverings including crowns) receiving surface for receiving one or more caps (and/or crowns or similar objects) thereon.

The healing period for any method or procedure described herein may vary from patient to patient and can be of any length of time. For example, the healing period can be two weeks, one month, six weeks, two months, ten weeks, three months, fourteen weeks, four months, eighteen weeks, five months, twenty-two weeks, six months, twenty-six weeks, seven months, thirty weeks, eight months, thirty-four weeks, nine months, thirty-eight weeks, ten months, forty-two weeks, eleven months, forty-six weeks, and a year.

In an embodiment, the implants and methods using the same, provide for a single or a multi-step process (e.g., periods of delay in between treatments and/or separate surgical procedures). In an embodiment, the implants and methods embodying features of the present invention provide for relatively immediate placement of the implant configured for integration with the patient's bone within the body, and in particular, in areas having bone deficiency. In an embodiment, the implants and methods embodying features of the present invention comprise a multi-step process where there are periods of delay and healing in between separate surgical procedures.

By way of example, in the case of the rig being implanted in the lower jaw of the patient, at least the lower edge, surface, or rim will include the bone fixation surface for affixation of the device to the lower jaw of the patient. The rig, at its front and/or back ends, may also include at least one or more bone fixation surface.

The rig may include, at the top edge or surface or rim (as for example the edge opposite the lower jaw bone and directed toward the roof of the mouth), a cap (or crown) receiving surface. The cap-receiving surface is configured for securely receiving thereon a cap or similar device, such as a dental crown.

In an embodiment, the rig at the upper surface includes at least one abutment surface, disposable between the rig and the cap, for receiving the dental cap thereon. The at least one abutment surface may be splinted rigidly as one piece with the rig or attachable to the rig by suitable means and structures including but not limited to adhesives, male/female attachments, screws and the like.

The rig may be custom designed using any number of suitable means such as three dimensional (3D) modeling software to fit the particular anatomical area of interest such as an edentulous area of the specific patient. Such design may be carried out upon imaging of the patient's anatomical area of interest using techniques and tools such as CT scan of the jaw. Upon completion of the design of the rig, the virtual design may be transformed into a physical structure/rig by way of suitable techniques such as 3D Laser Sintering printers, such as those available from Materialise, 3D systems.

In some embodiments of the method, the bio-compatible material may be of any type, percentage composition, combination, purity, strength and the like. The bio-compatible material may be of general biocompatibility, immunological biocompatibility, or bio-energetic biocompatibility. Any type of biocompatible material may be used, for example, composite filling, porcelain, aluminum oxide, gallium alloys, non-allergenic or non-toxic metals, amalgam, alloy, direct composite, indirect composite inlay/onlay, porcelain inlay/onlay, gold inlay/onlay, titanium inlay/onlay, gold or silver, non-precious alloys, zirconium oxide, titanium, and combinations thereof.

In an embodiment, the rig includes cavities or cells defined by a plurality of girders which in turn form a truss. The bone matter may fill in the cavities over time. In an embodiment, the rig is configured to include a relatively higher cavity or cell surface area to implant surface area for enhanced subsequent integration with the patient's bone. In an embodiment, the rig may be hyroxyapatite coated, plasma sprayed, or etched (e.g., chemically etched) to provide the increased bone/implant surface.

Rigs constructed according to the present invention, provide for enhanced bone conduction. The rigs employed as scaffolding structures, allow autogenous, allograft, and or xenograft bone graft substance or bone morphogentic protein to grown in and around the rig to replace the missing bone.

In an embodiment, the rig may be affixed to the bone, e.g., jaw bone, by suitable means such as screws, wires, intrusions into the jaw bone by drilling specific osteotomies to allow certain parts of the rig to endosseously integrate with the patient's body. In an embodiment, the rig will, in time, become a part of the patient's body as bone grows inside and around the rig's mesh-like structure.

The implants embodying features of the present invention may be implanted as a single stage implant procedure. In an embodiment, the abutments (or abutment surfaces) can be splinted as one part of the rig. Transitional or permanent prosthesis may also be disposed on the same day of the procedure.

In an embodiment, the rig may be placed initially in the patient's mouth, separated, from permanent abutments. In this embodiment, the rig may be placed in the mouth along with healing screws. This configuration may allow the bone to grow and integrate with the rig and to be covered at least substantially with soft tissue. Thereafter, after passage of sufficient time (e.g., 6 months), during the next stage of the procedure, healing screws are removed and healing abutments are placed in the rig to allow the placement of permanent abutments and prosthesis at, preferably, a later time.

The rig may be covered with resorbable or non-resorbable membrane, connective tissue, pericardium membrane, alloderm graft, or any other suitable material held in soft tissue coverage and to allow for a sufficiently effective protection of the rig and the bone graft.

As indicated earlier, the rig may be used in other implant reconstructive procedures in other suitable areas of the jaw or the anatomy all together, where bone will be necessary or useful to grow in certain shape, form, and/or volume. By way of example and not limitation, such other modalities include orthopedics, plastic surgery, oral and maxillofacial surgery, ENT (ear, nose, throat), or any other anatomical area and procedure which may benefit from the devices and methods of the present invention.

The above and other features of the present invention, which will become more apparent as the description proceeds, are best understood by considering the following Detailed Description in conjunction with the accompanying drawings, wherein like characters represent like parts throughout the several views.

BRIEF DESCRIPTION OF THE DRAWINGS

Non-limiting and non-exhaustive features of the present invention are described with reference to the following figures, wherein like reference numerals refer to like parts throughout the various figures.

DESCRIPTION OF THE DRAWINGS

The present invention relates to devices and methods for implanting an implantable device in a patient's body. In an embodiment, the device is a dental implant serving as a platform for placement of dental crowns and/or caps and/or fixed or removable prosthesis.

Features of an exemplary device and method for implanting the same, after it has been fabricated as described earlier, will be explained in reference to the following figures. It should be noted that either or both process and apparatus elements may be intended when referring to the following figures.

Figure 1:
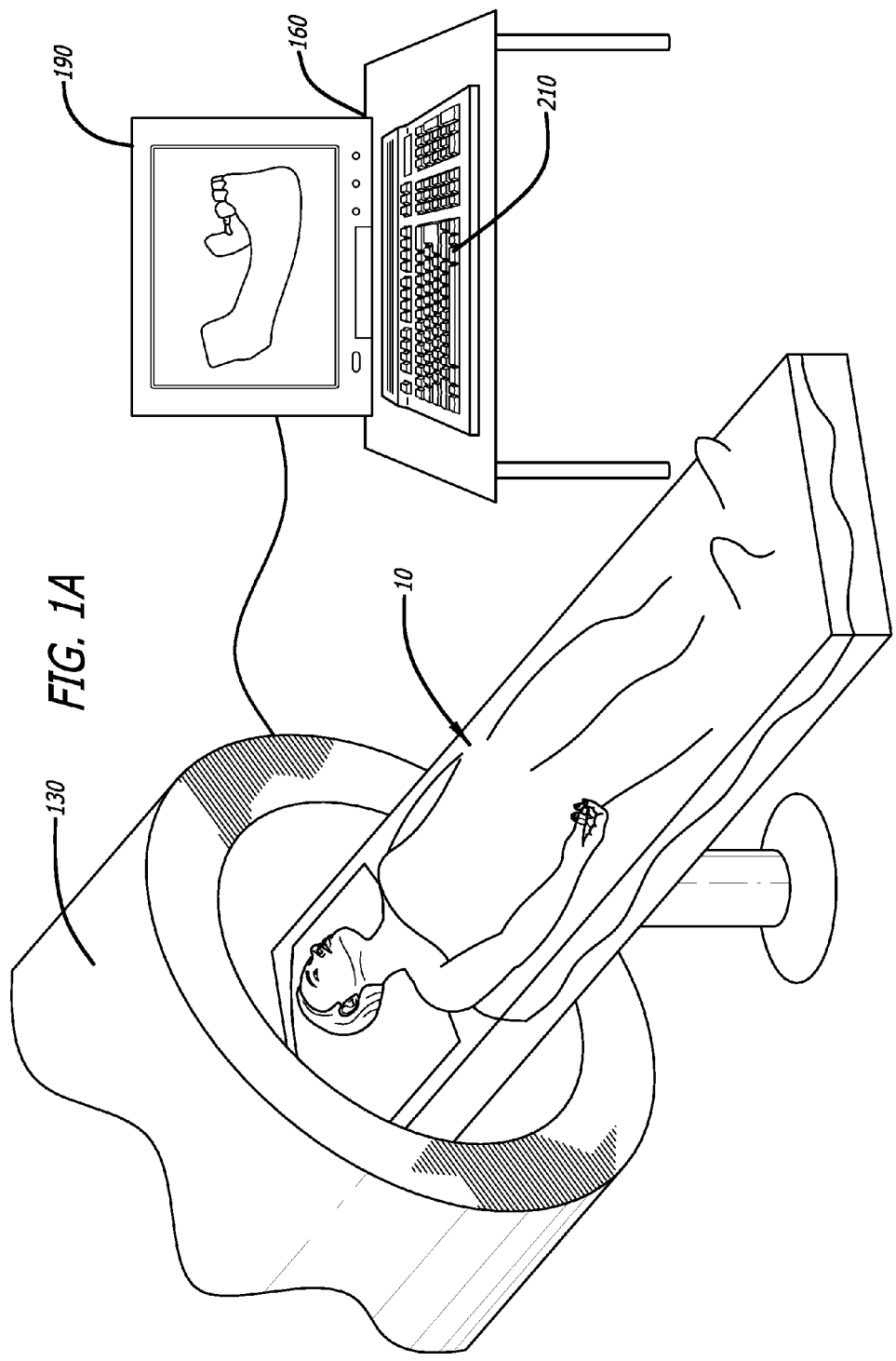
FIG. 1A is a simplified illustration of a patient undergoing imaging procedure.
FIG. 1B is a simplified illustration of the process for capturing the image of the patient's mouth and fabricating an implantable device having the features of the present invention.

Now referring to FIGS. 1A and 1B, a patient 10 is identified needing a dental implant. In an embodiment, the patient suffers from total or substantial bone loss in the jaw. The physician commissions a three dimensional image 11 of the patient's anatomical area of interest using a 3D scanning tool 130. The anatomical area of interest may be the patient's mouth requiring such implant. The image and related information may be captured on a data storage 160, either local or remote to the scanning tool. The image and related information may be displayed on a display 190 with a keyboard 210 providing the means for data and instructional communication between an operator and the scanning tool 130.

Once the image has been scanned, the image is used to create a virtual implantable device. The commissioning and design, as for example shown in 13 of FIG. 1B, of the suitable implant may include the use of any appropriate tool including computer modeling.

Figure 2:
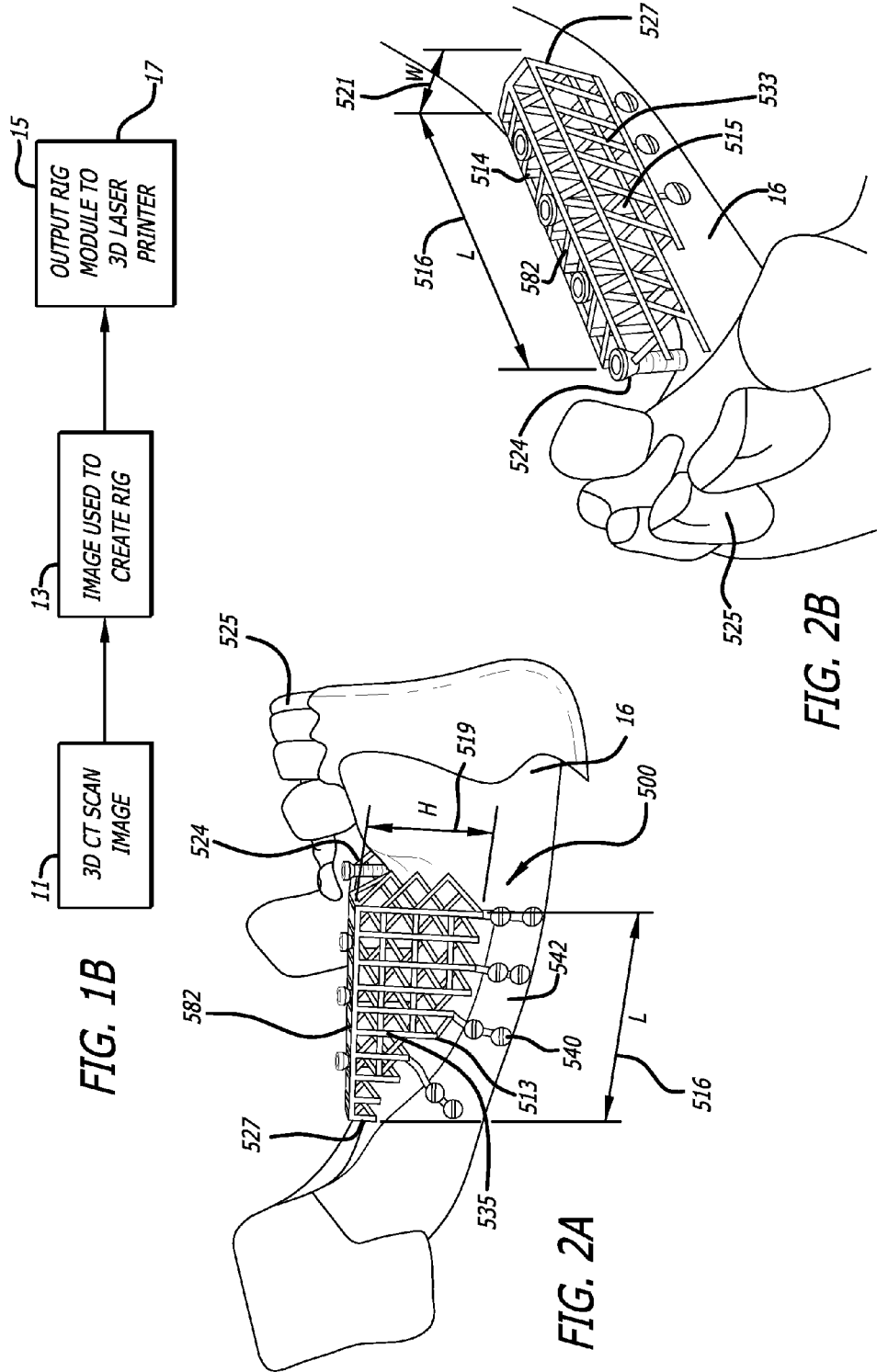
FIGS. 2A and 2B are simplified illustrations of an implantable device embodying features of the present invention disposed within a patient's mouth.

The fabrication of the implant is then commissioned, as for example shown in 15 of FIG. 1B. The virtual implantable device is thereafter used to create a 3D implantable device 500 (as shown in FIGS. 2A and 2B), using techniques such as 3D laser printing. The implant may be fabricated using other suitable methods, including, but not limited to, deposition or casting. As shown, a 3D laser printer 17 used to fabricate the implantable device 500.

3D printing is a form of additive manufacturing technology where a three dimensional object is created by laying down successive layers of material. 3D printers are generally faster, more affordable and easier to use than other additive manufacturing technologies. 3D printers offer product developers the ability to print parts and assemblies made of several materials with different mechanical and physical properties in a single build process. Advanced 3D printing technologies yield models that can serve as product prototypes. Using techniques and equipment such as 3D laser printers, great resolution, accuracy, and precision in the fabrication of the desired object can be obtained.

Thereafter, after appropriate examination of the fabricated implant, the implant using methods embodying the present invention will be affixed within the patient, e.g., patient's mouth.

Now referring to FIGS. 2A and 2B, an exemplary implantable device 500 is shown as disposed in a subject's mouth.

In an embodiment, the implantable device 500 includes a trabecular meshwork structure such as a rig 513 having a length 516, a height 519, a width 521, a front edge (or rim) 524, and back edge 527, an outer edge or surface 535, and an inner edge or surface 533. The rig 513 includes pluralities of girder-like structures 514 defining a plurality of cavities 515 therebetween. It should be noted that the term girder-like is not intended to be limited to elements which may form traditional triangular truss structures or elements and the network may take any suitable form or geometry as for example, the truss-like structures having curved elements such as struts in a cardiovascular stent. It should further be noted that the nouns describing the various parts of the device are used for ease of reference and are as defined by the present inventor. By way of example, as used herein and as positioned in the lower jawbone 16 of a patient's mouth, the front edge 524 refers to the side closest to the patient's lips; back edge 527 refers to the edge opposite the front edge; outer edge surface 535 to the side of the device facing the cheek of the patient; the inner surface 533 refers to the side of the device opposite the outer surface; the length 516 refers to the dimension extending from the front edge (e.g., front teeth 525) to the back edge 527 (toward the molar tooth); height 519 refers to the dimension extending vertically in the direction from the lower jaw toward the roof of the mouth; width 521 refers to the dimension extending between the outer surface and the inner surface. It should be appreciated, however, that the devices of the present invention are not limited by these nouns and are adaptable for use in any suitable part of the mount or other anatomical areas of the patient.

Figure 13:
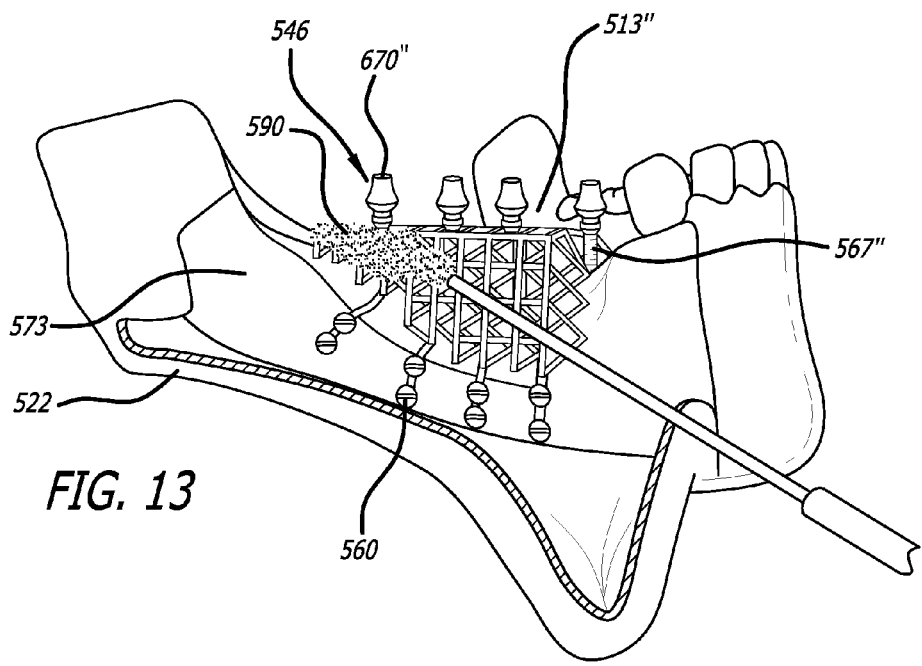
FIG. 13 is a simplified illustration of a step in a process for disposing an implantable device embodying features of the present invention in a patient's mouth, showing the application of bone graft substance onto and/or within cavities of the device, with abutments being integrated with the rig.
Figure 14:
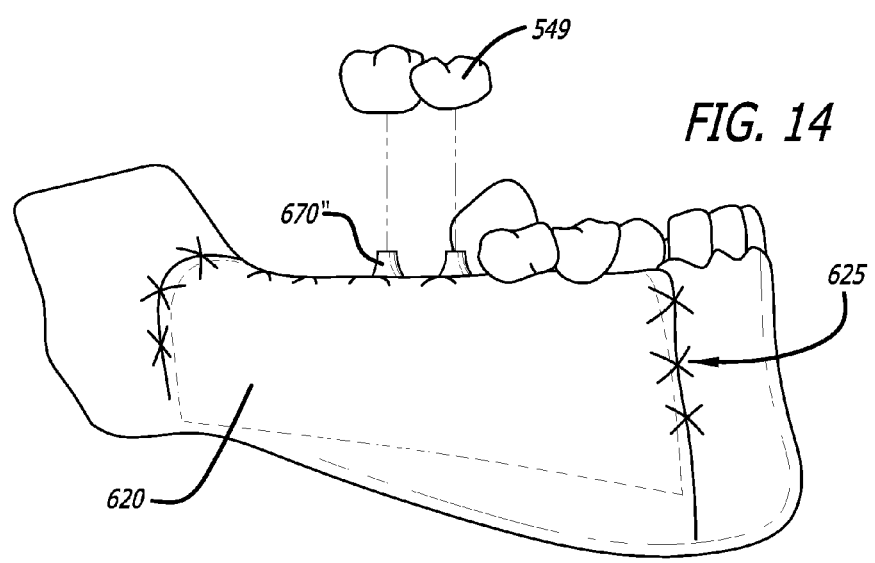
FIG. 14 is a simplified illustration of a step in a process for implanting the device of FIG. 13 in a patient's mouth, showing the suturing of the soft tissue flap.
Figure 15A:
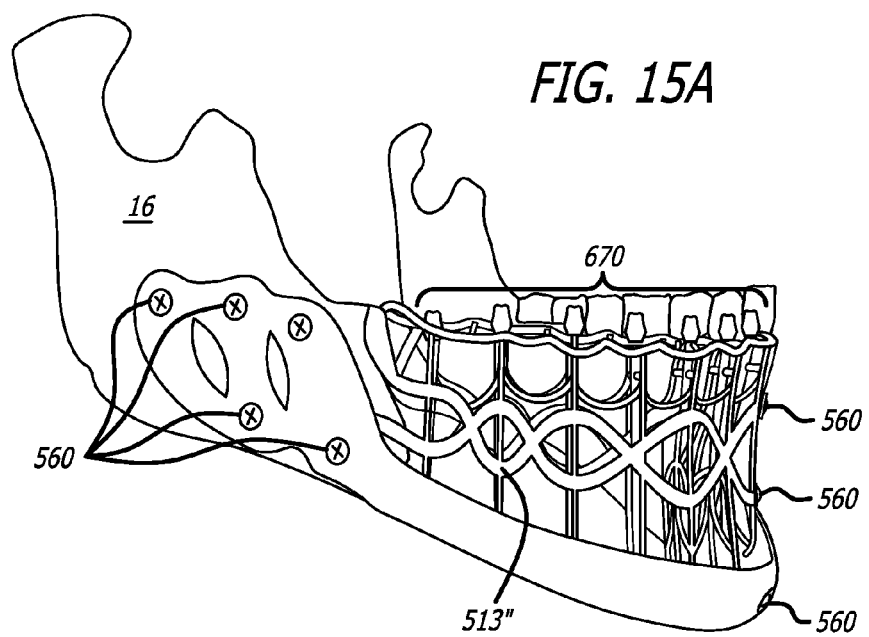
FIGS. 15A and 15B are simplified side views of steps in a process for replacing bone and restoring function when the whole body of mandible or whole segment of the mandible is missing due to various reasons such as cancer, gunshot, facial trauma, etc.
Figure 15B:
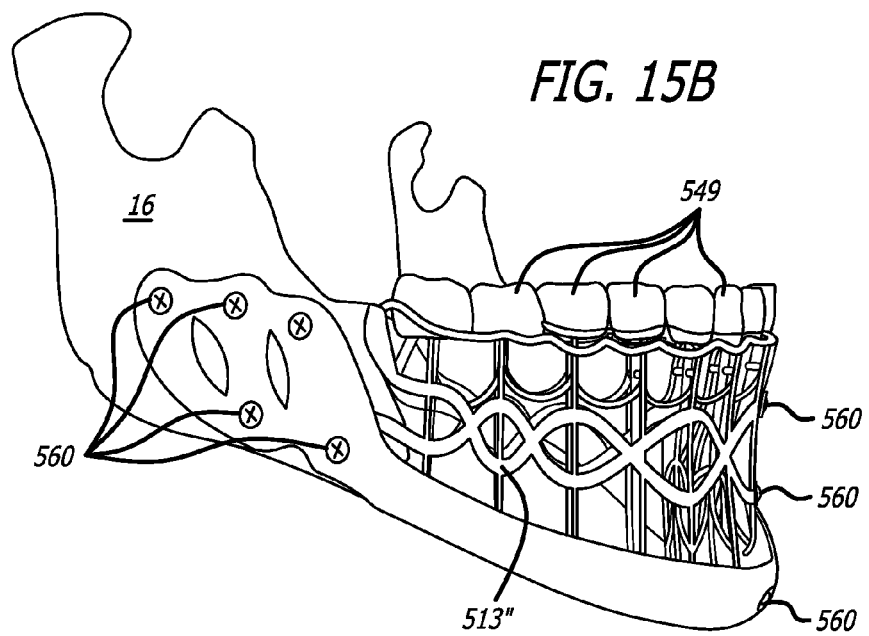
Figure 16A:
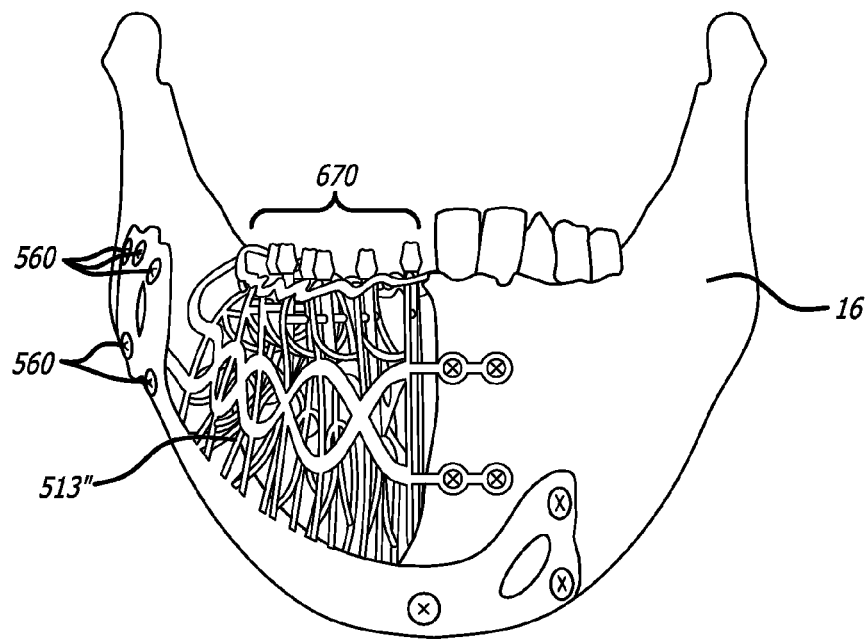
FIGS. 16A and 16 B are front views of illustrations of FIGS. 15A and 15B.
Figure 16B:
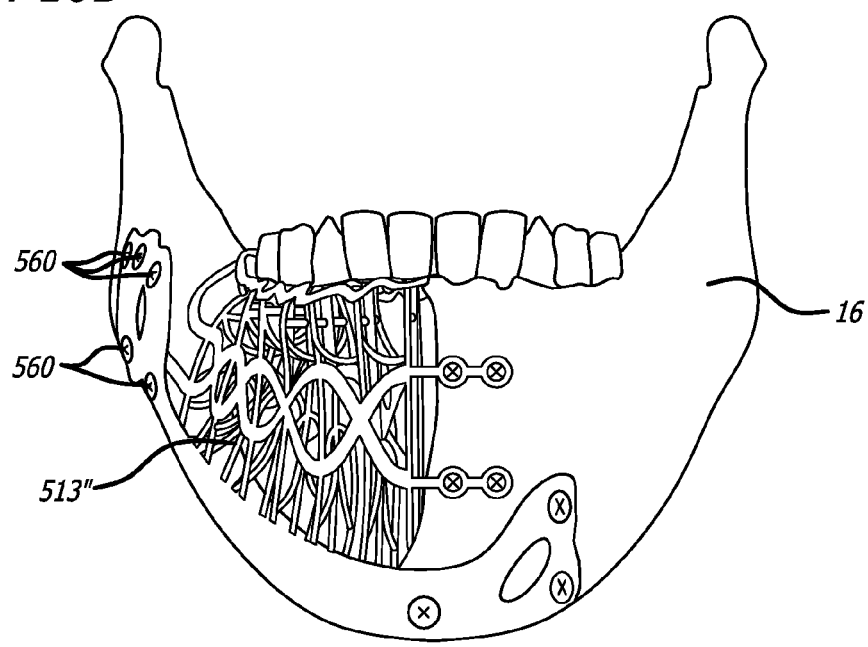
Figure 17A:
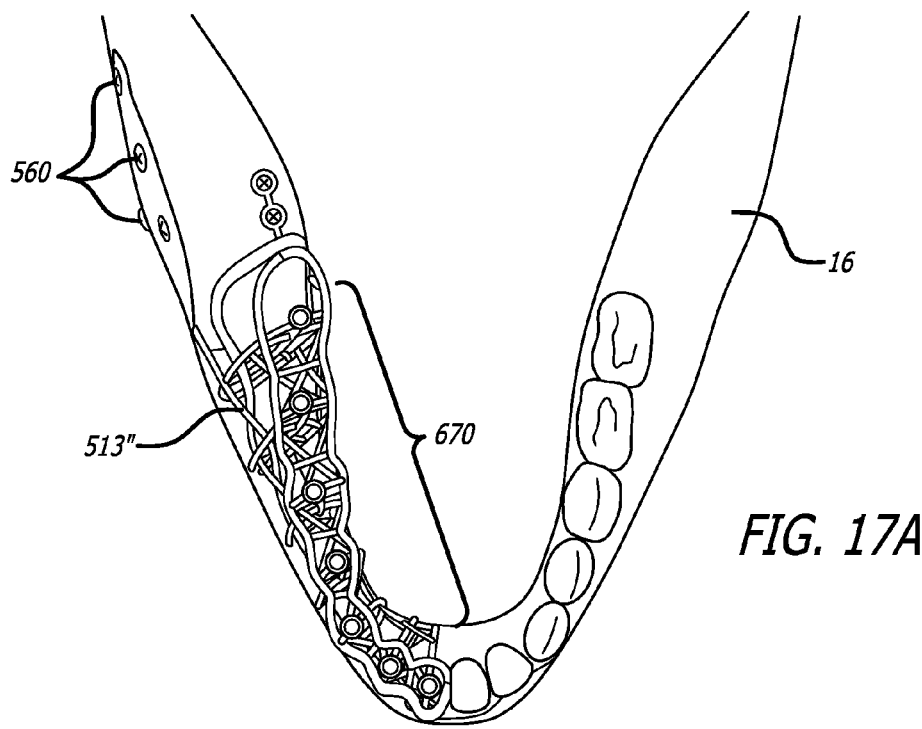
FIGS. 17A and 17 B are top views of illustrations of FIGS. 15A and 15B.
Figure 17B:
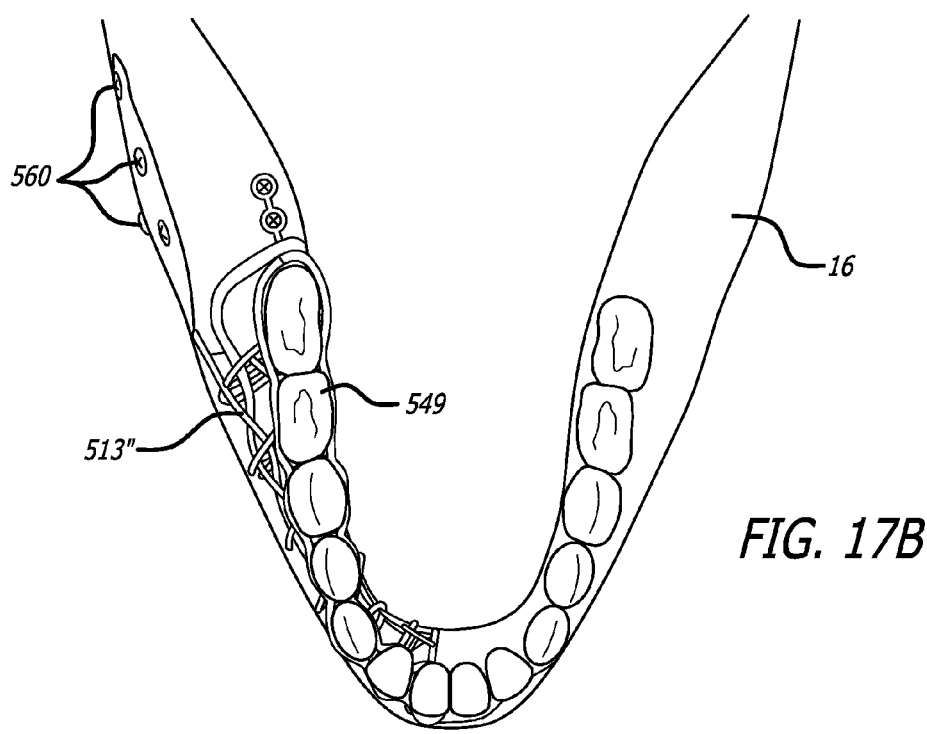
Figure 18A:
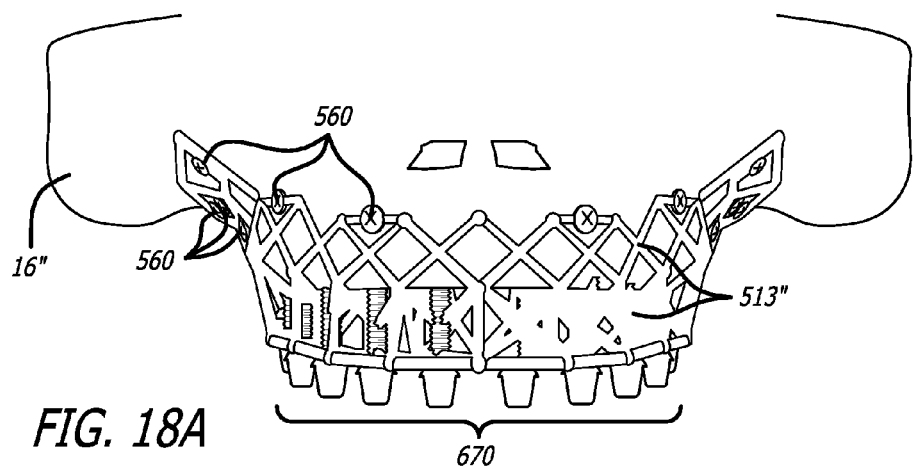
FIGS. 18A and 18B are simplified front views of steps in a process for restoring the aesthetic and function in atrophic jaw where all the teeth are missing.
Figure 18B:
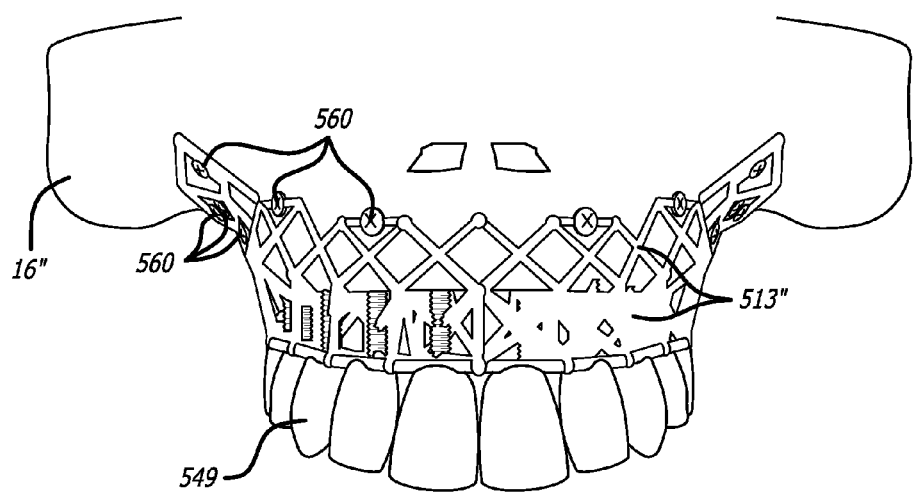
Figure 19A:
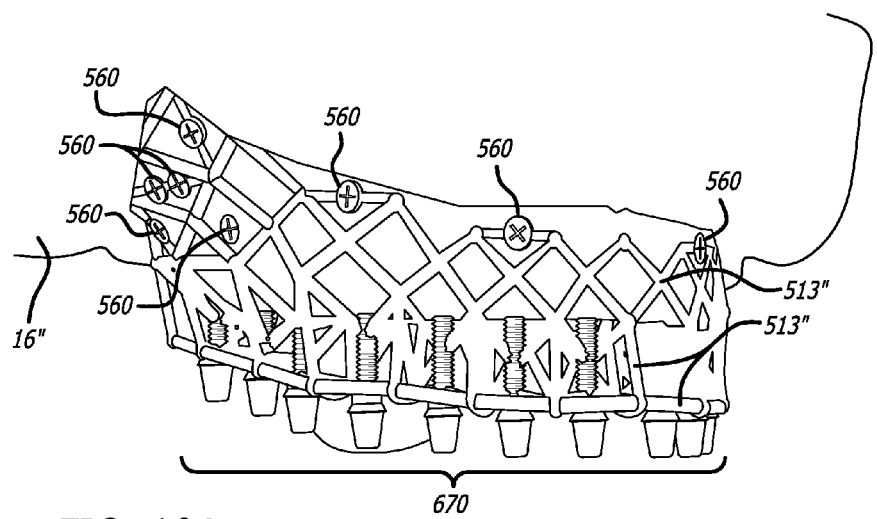
FIGS. 19A and 19 B are side views of illustrations of FIGS. 18A and 18B.
Figure 19B:
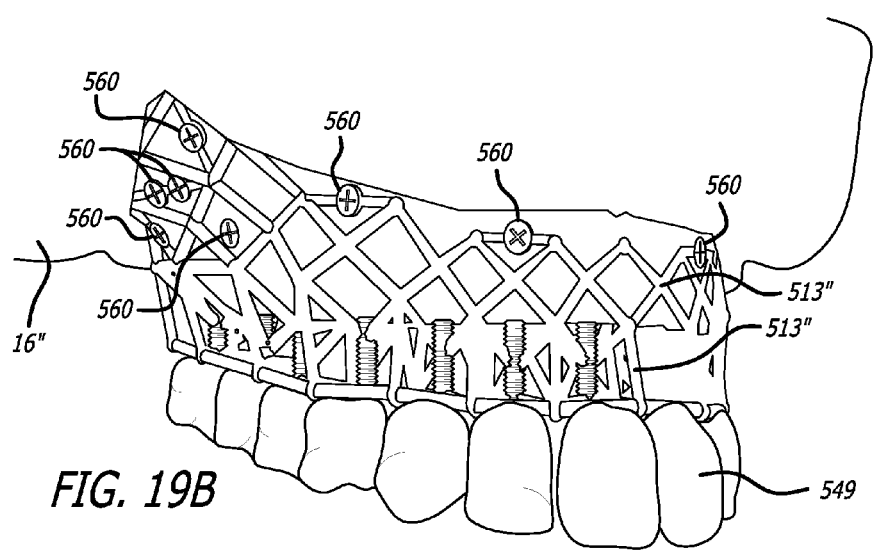
Figure 20A:
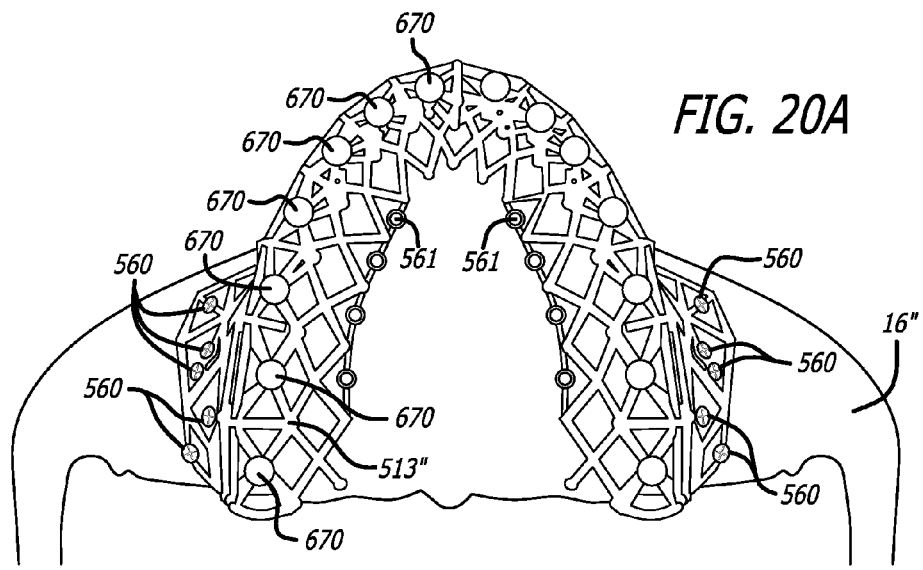
FIGS. 20A and 20 B are top (occlusal) views of illustrations of FIGS. 18A and 18B.
Figure 20B:
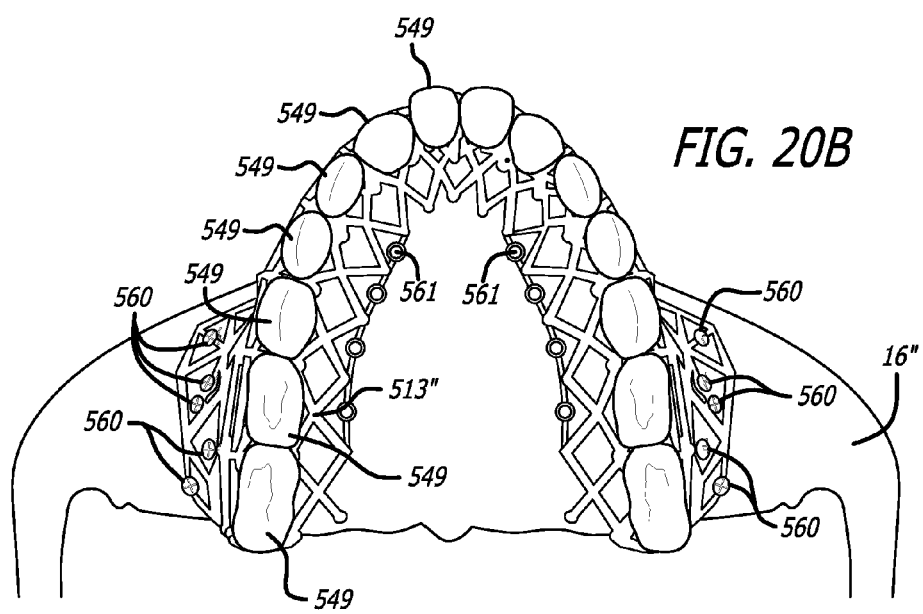

The implant 500 includes at least one bone fixation feature 540 for being operatively attachable to a bone surface 542 of the patient, and at least one cap (or similar coverings including crowns) receiving feature 546 (see for example, FIG. 13) for receiving one or more caps 549 (and/or crowns) thereon (See FIG. 14). As shown in FIGS. 2A and 2B, the at least one bone fixation feature 540 is configured for being fixedly attachable to the lower jawbone 16 of the patient and the at least one cap receiving feature 546 is opposite the at least one fixation feature 540.

Figure 3:
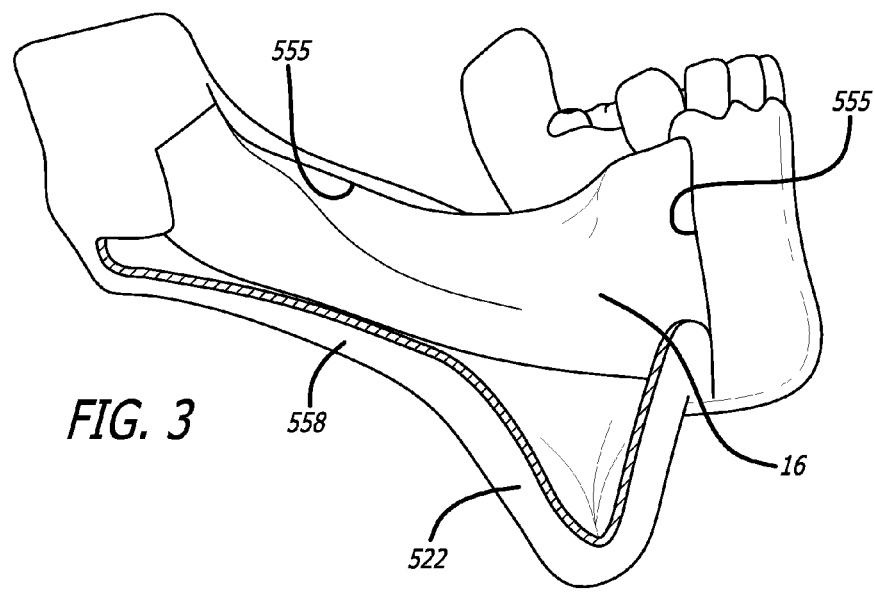
FIG. 3 is a simplified illustration of a process for exposing a patient's jaw bone by reflecting the gums and oral mucosa covering the bone.
Figure 4:
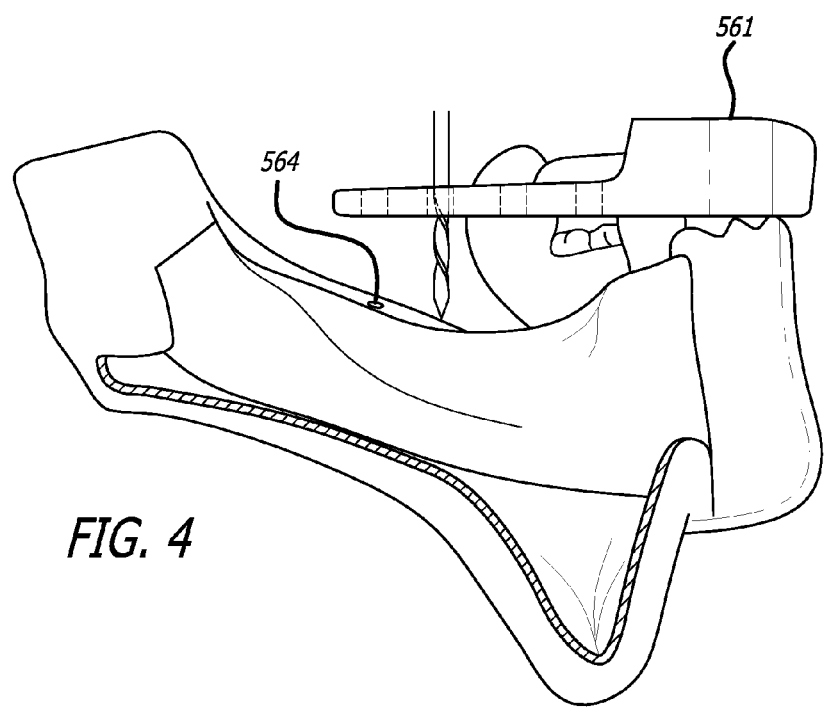
FIG. 4 is a simplified illustration of a step in a process for disposing an implantable device embodying features of the present invention in a patient's mouth, showing the disposal of a surgical guide in the patient's mouth.

Now referring to FIGS. 3 and 4, a gum 522 is incised by way of an incision 555 and reflected 558 exposing the jawbone 16. A surgical guide 561 is positioned on the teeth. Osteotomes 564 are drilled through the surgical guide 561 into the jawbone 16. The surgical guide 561 is thereafter removed.

Figure 5:
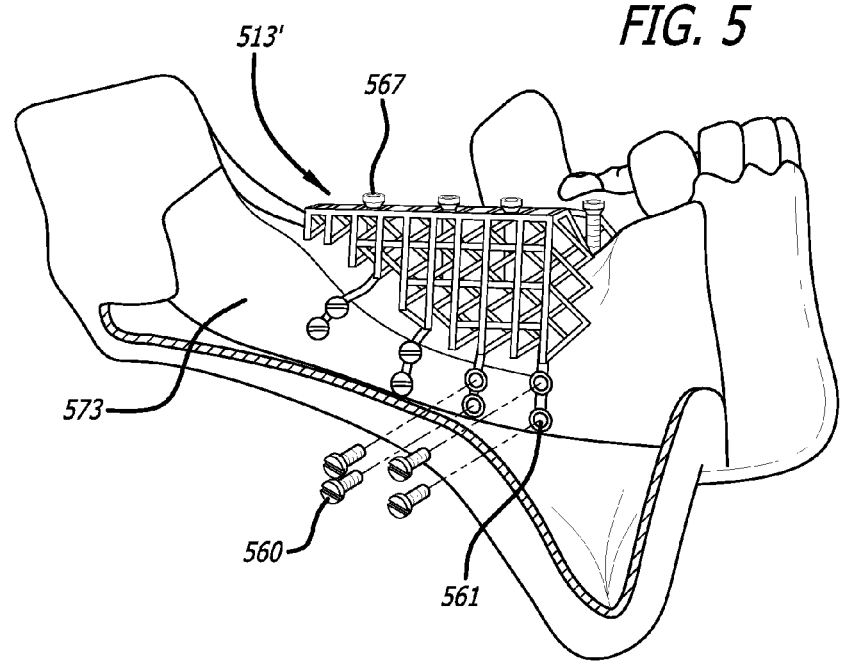
FIGS. 5 and 6 are simplified illustrations of steps in a process for disposing an implantable device embodying features of the present invention in a patient's mouth, showing the disposal of a device in the patient's mouth.
Figure 6:
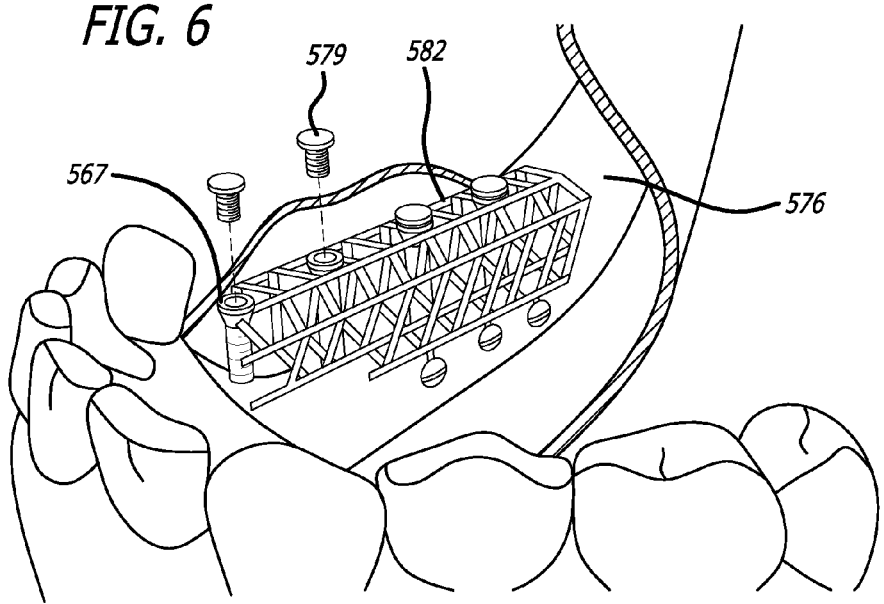

As shown in FIGS. 5 and 6, a rig 513', such as a titanium rig, and incorporated with root-form implant 567 is then placed on the jawbone 16. Fixating elements 560, such as fixating screws, are used to fixate the rig 513' onto the jawbone 16 on either or both the front and back of the jawbone. The fixating may occur in one or more places along the jawbone as appropriate. By way of example, one or more fixating screws 560 may be positioned through fixation ports 561 in outer surface 573 of the jawbone, on the inner surface 576 of the jawbone, front-portion of the jawbone, and/or backside-portion of the jawbone, or any other portion as may be necessary. One or more healing elements such as healing screws 579 are positioned in the rig 513'. As shown in FIG. 6, a plurality of healing screws 579 are positioned on the top surface 582 of the rig (or the bottom surface if the rig were disposed on the upper jaw). The rig is secured in place as can be seen from FIGS. 5 and 6, on both the outer and the inner potions of the jawbone.

Figure 7:
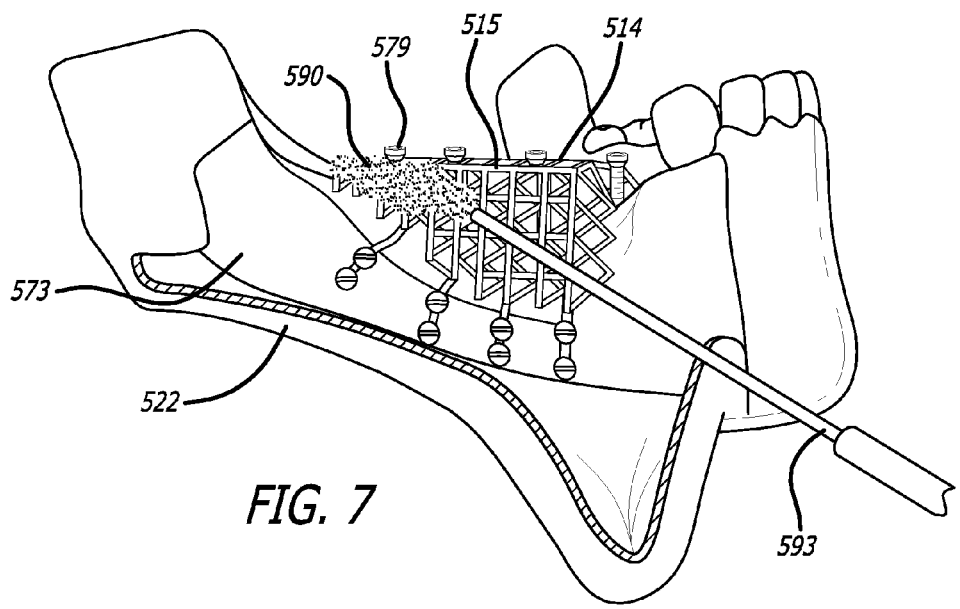
FIG. 7 is a simplified illustration of a step in a process for disposing an implantable device embodying features of the present invention in a patient's mouth, showing the application of bone graft substance onto and/or within cavities of the device.
Figure 8:
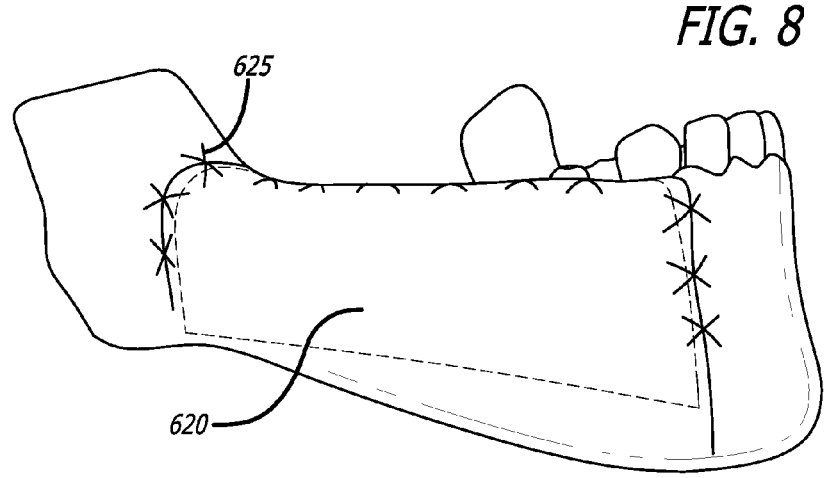
FIG. 8 is a simplified illustration of a step in a process for disposing the device of FIG. 7 in a patient's mouth, showing the suturing of the flap.

Bone graft substance 590, as can be seen in FIG. 7, is placed in and around the rig using appropriate tools such as surgical spatula 593. In the embodiment, as shown, the bone graft substance 590 is particularly placed inside the cavities/cells 515 formed by the girders 514. As shown in FIG. 7, the bone graft substance covers at least substantially the inside and the outside of the rig. The rig provides scaffold, where the bone graft will conduce bone growth. Membrane 620 is placed over, at least a substantial portion, of the rig to cover the rig and the bone graft substance. In the embodiment shown, the membrane at least substantially covers the healing screws 579. The gum 522 is then sutured in place using sutures 625 or other similar elements.

Figure 9:
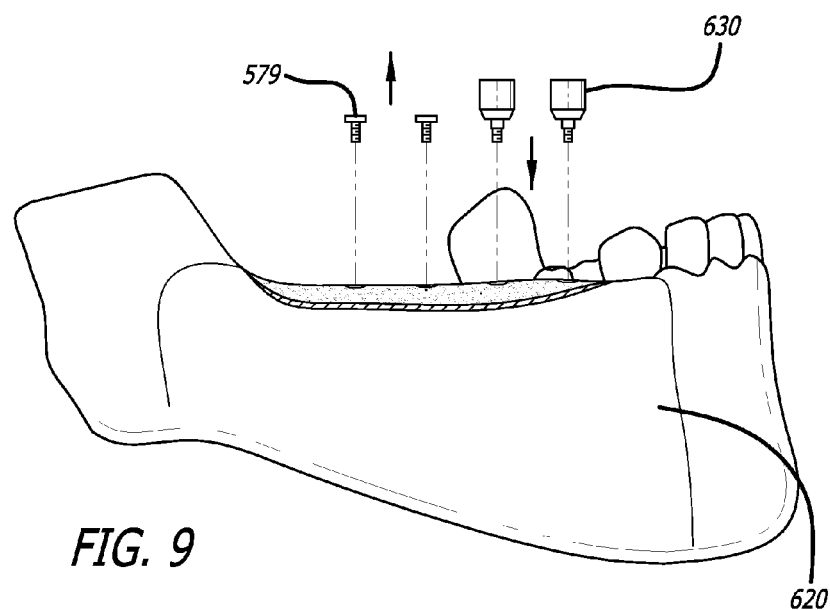
FIG. 9 is a simplified illustration of a step in a process for implanting the device of FIG. 8 in a patient's mouth, showing the removal of healing screws and placement of healing abutments.
Figure 10:
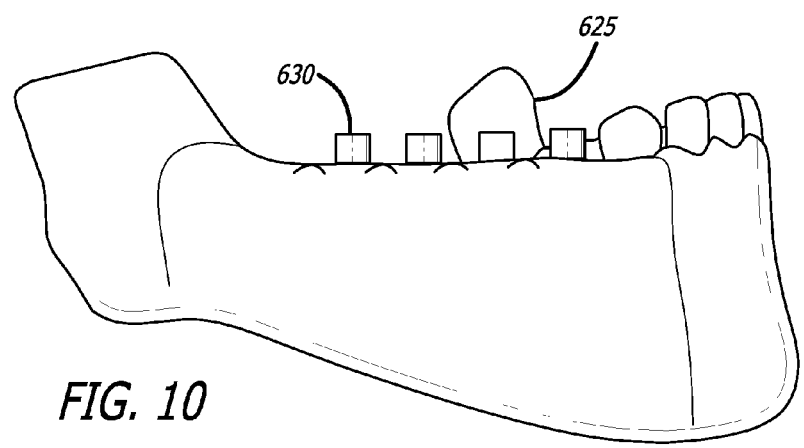
FIG. 10 is a simplified illustration of a step in a process for implanting the device of FIG. 9 in a patient's mouth, showing healing abutments in place.

Now referring to FIGS. 9 and 10, after passage of suitable period of time, for example 6 months, the healing screws 579 are exposed and removed. Healing abutments 630 are placed on the rig 513' where the healing screws 579 were previously located.

Figure 11:
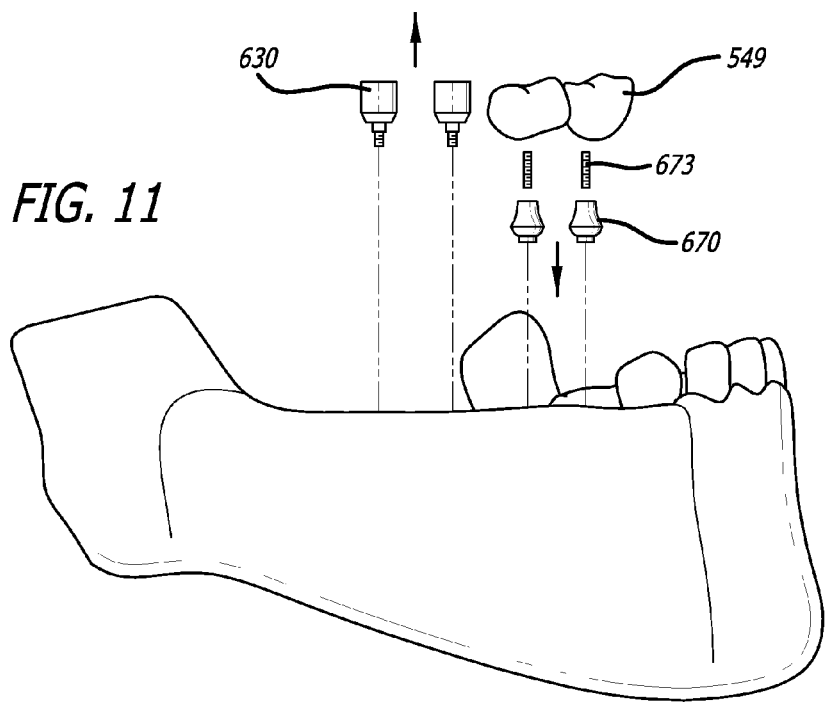
FIG. 11 is a simplified illustration of a step in a process for implanting the device of FIG. 10 in a patient's mouth, showing the removal of healing abutments.
Figure 12:
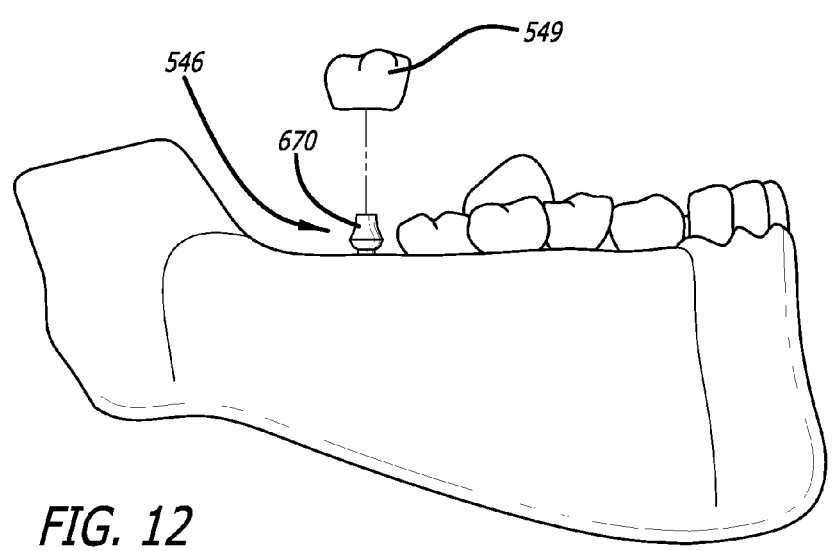
FIG. 12 is a simplified illustration of a step in a process for implanting the device of FIG. 11 in a patient's mouth, showing the placement of crowns.

Now referring to FIGS. 11 and 12, after the passage of suitable period of time, for example 1 month, the healing abutments 630 are removed and permanent abutments 670 and crowns 549 are placed onto the rig 513'. Abutment fixating screws 673, may be used to secure the permanent abutments 670 onto the rig 513. The sutures may also be removed at this time (or the sutures may of the disintegratable or resorbable type).

In an exemplary embodiment, similar to the method generally described above, features of which are generally shown in FIGS. 13 and 14, after the completion of steps generally shown in FIG. 4, a rig 513" incorporated with root-form implant 567" and abutments 670" is placed on the jawbone 16. Fixating screws 560 are used to fixate the rig 513" on the jawbone. Bone graft substance 590 is placed in and around the rig similar to that describe in relation to FIG. 7. The rig 513" provides a scaffold where the bone graft will conduce bone. Membrane 620 is placed on top of the rig (and the incorporated abutments") and the bone graft. The gum is sutured in place using sutures 625. Finally the crowns 549 are disposed on the abutments 670", all during the same surgical procedure. The rig will eventually fuse with the jawbone over time.

Now referring to FIGS. 15A, 15B, 16A, 16B, 17A and 17B, an exemplary implantable device 500 is shown as disposed in a patient's mouth to replace a missing segment of the lower jaw (mandible) which may have been a result of any number of circumstances such as cancer, gun shot wound, or the like.

As shown, the rig 513", incorporated with root-form implant 567" and abutments 670", is disposed on the mandible bone 16, after a portion of the gum has been excised and reflected. Fixating screws 560 are used to fixate the rig 513" on the jawbone. Bone graft substance 590 is placed in and around the rig similar to that describe in relation to FIGS. 13 and 14. The rig 513" provides a scaffold where the bone graft will conduce bone. A girder of the scaffold is undulating along an outer edge of the scaffold. Membrane 620 (not shown) is placed on top of the rig (and the incorporated abutments") and the bone graft. The gum is sutured in place using sutures 625. Finally the crowns 549 are disposed on the abutments 670", all during the same surgical procedure. The rig will eventually fuse with the jawbone over time. In the alternative, the crowns 549 may be pre-disposed on the abutments 670" prior to the rig being disposed on the jawbone. In the embodiment shown, the lower portion of the implant may have a sufficiently large surface area in order to provide the necessary affixation of the implant to the jawbone.

Now referring to FIGS. 18A, 18B, 19A, 19B, 20A and 20B, an exemplary implantable device 500 is shown as disposed in a patient's mouth to replace missing teeth of a patient with severe to moderate bone loss on the edentulous upper jaw 16".

Bone Grafts

Bone grafts may be used in combination with the method and/or device herein. Bone grafts may also be used before and/or after the method and/or device described herein. There are several types of bone grafts, any of which may be used at any time sequence or frame of time in reference to the present invention. Bone grafts may be used wherein the bone to be grafted to the jaw is taken, or harvested, from the patient's own body. The area where the bone is harvested from, known as the donor site, is usually the mouth or the hip. This is the patient's own bone and is very compatible with his/her body. Autografts are generally the best graft technique and usually result in the greatest regeneration of missing jawbone.

Allografts are taken from human donors. Bone obtained in this manner undergoes rigorous tests and sterilization. The patient's body converts the donor bone into the patient's natural bone, thereby rebuilding his/her resorbed jawbone. Xenografts are harvested from animals. The animal bone, most commonly bovine (cow), is specially processed to make it biocompatible and sterile. It acts like a filler which in time the patient's body will replace with natural bone. After this replacement process is complete, dental implants may be placed to support the teeth. Alloplastic grafts are inert, man-made synthetic materials. The modern artificial joint replacement procedure uses metal alloplastic grafts. For bone replacement a man-made material that mimics natural bone is used. Most often it is a form of calcium phosphate. Depending on how it is made, it may be resorbable or non-resorbable. That is, the patient's body may or may not replace the alloplastic graft with the patient's natural bone. In those cases where it is not replaced, it acts as a lattice or scaffold upon which natural bone is built. In either case, the end result is to create enough bone for the placement of dental implants. Recently, recombinant human bone morphogenetic protein (e.g., available from Medtronic Corporation) has been used to create bone by inducing the stem cells to differentiate to osteoblast (bone forming cells) to form new bone. Other types of bone grafting using recombinant DNA technology such as, for example, growth factors and/or morphogens may also be used.

Root-Form Implants

Root-form implants may be incorporated as part or parts of the method and/or device herein. Root form implant, when they are incorporated in the device or rig could be partially placed inside the present bone when the bone volume allows to aid in the primary retention and fixation of the device. Root-form implants may also be used in areas adjacent to where the device is placed before and/or after the method and/or device described herein. There are several types of root-form implants, any of which may be used at any time sequence or frame of time in reference to the present invention. Root-form implants may be the closest in shape and size to the natural tooth root. They are commonly used in wide, deep bone to provide a base for replacement of one, several or a complete arch of teeth. After application of anesthetic, the dentist will expose the area of the jawbone to be implanted and prepare the bone to accept the implant. The number of incisions and bone preparations depends upon the number of implants (and teeth) being placed. The implant is carefully set into place and the gums are closed with several stitches. The healing period usually varies from patient to patient and can be of any time length. For example, the healing period can be two weeks, one month, six weeks, two months, ten weeks, three months, fourteen weeks, four months, eighteen weeks, five months, twenty-two weeks, six months, twenty-six weeks, seven months, thirty weeks, eight months, thirty-four weeks, nine months, thirty-eight weeks, ten months, forty-two weeks, eleven months, forty-six weeks, and a year. During this time, osseointegration occurs. The bone grows in and around the implant creating a strong structural support. In fact, this bond can be even stronger than the original tooth. When healing is complete, the implant is uncovered and an extension or abutment is attached to it. Now the implant and abutment act as a solid unit ready to support the new tooth or teeth.

Plate-form implants are usually used when the bone is so narrow that it may not be suitable for the root-form implant and the area is not suitable for bone grafting. The plate-form implant is flat and long so it can fit into the narrow jawbone. After application of anesthetic, the dentist will expose the area of the jawbone to be implanted and prepare the bone to accept the shape of the implant. The number of incisions depends upon the number of implants being placed. The implant is carefully set into place and the gums are closed with several stitches. Like root-form implants, there is usually a healing period for osseointegration, although some plate form implants are designed for immediate restoration. The plate form implant or implants could be incorporated as part or parts of the rig. The plate form could be implanted in the area adjacent to the area where the device is implanted before or after the device is implanted.

With very advanced jawbone resorption there may not be enough bone width or height for the root-form or plate-form implant. In these cases the subperiosteal implant may be prescribed. The subperiosteal implant is custom made and designed to sit on top of the bone, but under the gums. There are two methods for its placement.

In the dual surgery method, after application of anesthetic, the dentist will expose the jawbone and take an impression or model of the bone using special materials. This model is used by a dental laboratory to carefully create the custom implant to fit the patient's jaw. A second procedure is then carried out where the jawbone is exposed and the implant placed. The gums are closed with several stitches and replacement teeth are put into place.

In the single surgery method the dentist will order a special CAT scan of the patient's jawbone. Using the CAT scan data and advanced computer modeling techniques, a model of the jawbone is constructed. This model is used by a dental laboratory to fabricate the custom subperiosteal implant to fit the patient's jaw. A surgical procedure is then carried out where the jawbone is exposed and the implant placed. The gums are closed with several stitches and the replacement teeth are put into place.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented methods and/or processes as a particular sequence of steps. However, to the extent that the methods or processes do not rely on the particular order of steps set forth herein, the methods or processes should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

That which is claimed:

1. An implantable dental device for implanting within a subject's mouth, comprising:
    a 3 dimensional trabecular meshwork structure configured to promote bone growth and having a plurality of interconnected cells, at least a portion of the cells forming a plurality of vertically aligned cells with at least a portion of the cells configured for receiving bone graft material therein, the meshwork structure having a length, a height, a width, a first end, and a second end;
    at least one root-form implant formed integral with the meshwork structure, the root-form implant integrated with the meshwork structure prior to placement within the subject's mouth, a girder of the meshwork structure undulating along an outer edge of the meshwork structure;
    at least one fixating surface, extending directly from the undulating girder of the meshwork structure and configured to accept at least one fixating element, for operatively attaching the meshwork structure to the subject's jawbone; and
    at least one prosthesis receiving surface disposed adjacent a corresponding root-form implant, the prosthesis receiving surface configured for receiving a corresponding prosthesis thereon.

2. The device of claim 1, wherein the length of the meshwork structure is nominally defined by a distance between first end and second end of the structure, and ranges from about 5 mm to about 200 mm.

3. The device of claim 1, wherein the height of the meshwork structure is nominally defined by a distance between a lower rim and an upper rim of the meshwork structure, and ranges from about 1 mm to about 60 mm.

4. The device of claim 1, wherein the plurality of cell structures comprises a matrix having a depth and height which ranges from about 1 to about 9 cells, and from about 9 to about 1 cell, respectively.

5. The device of claim 1, wherein each cell has an inner surface area ranging from about 50 microns to about 10 mm.

6. The device of claim 1, wherein the ratio of the total inner area of the cells to the total surface area of the meshwork structure ranges from about 10% to about 90%.

7. The device of claim 1, wherein the at least one prosthesis receiving surface includes at least one abutment receiving surface for receiving an abutment thereof.

8. An implantable dental device for implanting within a subject's mouth, comprising:
- a 3 dimensional trabecular meshwork structure configured to promote bone growth and having a plurality of interconnected cells configured for receiving bone graft material therein, the structure having a length, a height, a width, a first end, and a second end, the structure configured for permanent placement within the subject's mouth;
- a plurality of root-form implants formed integral with the structure prior to placement within the subject's mouth, a girder of the meshwork structure, undulating along an outer edge of the structure, coupled to at least one fixating surface extending directly from the undulating girder;
- the at least one fixating surface configured to accept one or more fixating elements for operatively and fixedly attaching the structure to the subject's jawbone; and
- a plurality of prosthesis receiving surfaces, each of the prosthesis receiving surfaces disposed adjacent a corresponding root-form implant, for receiving a corresponding number of prosthesis thereon.

9. The device of claim 8, wherein at least some of the plurality of the prosthesis receiving surfaces includes a corresponding abutment receiving surface for receiving an abutment thereon.

* * * * *